US009750432B2

(12) United States Patent
Nahum et al.

(10) Patent No.: US 9,750,432 B2
(45) Date of Patent: Sep. 5, 2017

(54) METHOD FOR THE AUTOMATED AND ASSISTED ACQUISITION OF ANATOMICAL SURFACES

(71) Applicant: MEDTECH S.A., Chemin de Borie (FR)

(72) Inventors: Bertin Nahum, Baillargues (FR); Fernand Badano, Villeurbanne (FR); Pierre Maillet, Sainte Aunes (FR); Alexander Habermeier, Montpellier (FR); Patrick Dehour, Crespian (FR)

(73) Assignee: MedTech S.A., Montpellier (FR)

( * ) Notice: Subject to any disclaimer, the term of this patent is extended or adjusted under 35 U.S.C. 154(b) by 0 days.

(21) Appl. No.: 14/949,822

(22) Filed: Nov. 23, 2015

(65) Prior Publication Data
US 2016/0073933 A1 Mar. 17, 2016

Related U.S. Application Data

(63) Continuation of application No. 13/810,186, filed as application No. PCT/FR2011/051747 on Jul. 20, 2011, now Pat. No. 9,237,861.

(30) Foreign Application Priority Data

Aug. 4, 2010 (FR) ...................................... 10 56428

(51) Int. Cl.
*A61B 5/107* (2006.01)
*A61B 5/1171* (2016.01)
(Continued)

(52) U.S. Cl.
CPC .......... *A61B 5/1077* (2013.01); *A61B 5/0064* (2013.01); *A61B 5/1176* (2013.01);
(Continued)

(58) Field of Classification Search
CPC ......... A61B 8/483; A61B 8/00; A61B 5/1077; A61B 8/4477; A61B 17/645;
(Continued)

(56) References Cited

U.S. PATENT DOCUMENTS 4,549,540 A 10/1985 Caspari et al.
4,722,056 A 1/1988 Roberts et al.
(Continued)

FOREIGN PATENT DOCUMENTS

DE 102008022924 A 11/2009
EP 1680007 B1 4/2013
(Continued)

OTHER PUBLICATIONS

Ruby Shamir, Miniature robot system for keyhole neurosurgery, A thesis submtted in fulfillment of the requirements for the degree of Master of Science, The Selim and Rachel Benin School of Engineering and Computer Science, The Hebrew University of Jerusalem, Nov. 13, 2005. Total 63 pages.*
(Continued)

*Primary Examiner* — Haixia Du
(74) *Attorney, Agent, or Firm* — Schwegman Lundberg & Woessner, P.A.

(57) ABSTRACT

The method for the automated and assisted acquisition of anatomical surfaces includes a first acquisition of the surfaces undertaken in order to create a first numerical model and a perioperative second acquisition undertaken by scanning the surfaces in order to create a second numerical model for identifying the coordinates of the surfaces. The surfaces are supported by a robotic arm; and then the models are brought into correspondence by resetting. The scanning in the second acquisition includes making a preliminary identification of the coordinates of noteworthy points on the surfaces manually, assisted by the robotic arm, and the identifying parts a the points, in order to construct a reference frame and to determine a scanning region; creating an intermediate model from the reference frame and at least one of the points; preliminary resetting the first model with the
(Continued)

second model; and automatically scanning the determined zone.

8 Claims, 1 Drawing Sheet

(51) Int. Cl.
  *G06F 19/00* (2011.01)
  *G06K 9/00* (2006.01)
  *A61B 5/00* (2006.01)
  *A61B 90/00* (2016.01)
  *A61B 34/20* (2016.01)
(52) U.S. Cl.
  CPC .......... *A61B 90/361* (2016.02); *G06F 19/321* (2013.01); *G06F 19/3481* (2013.01); *G06K 9/00281* (2013.01); *A61B 34/20* (2016.02); *A61B 2034/2065* (2016.02); *A61B 2090/373* (2016.02); *A61B 2576/02* (2013.01)
(58) Field of Classification Search
  CPC ........... A61B 2017/00017; A61B 2017/00022; A61B 17/7001; A61B 34/30; A61B 34/10; A61B 34/70; A61B 5/055; A61B 34/20; A61B 2034/107; A61B 2090/363; A61B 5/0064; Y10T 74/20305; G06T 7/004; G06T 7/20; G06T 7/001; G06T 7/0028; H04N 1/00002; G01B 7/31
  See application file for complete search history.

(56) References Cited

U.S. PATENT DOCUMENTS

| | | | |
|---|---|---|---|
| 4,913,413 | A | 4/1990 | Raab |
| 5,383,454 | A | 1/1995 | Bucholz |
| 5,389,101 | A | 2/1995 | Heilbrun et al. |
| 5,403,319 | A | 4/1995 | Matsen, III et al. |
| 5,603,318 | A | 2/1997 | Heilbrun et al. |
| 5,799,055 | A | 8/1998 | Peshkin et al. |
| 5,871,018 | A | 2/1999 | Delp et al. |
| 5,976,122 | A | 11/1999 | Madhani et al. |
| 6,033,415 | A | 3/2000 | Mittelstadt et al. |
| 6,167,292 | A | 12/2000 | Badano et al. |
| 6,226,548 | B1 | 5/2001 | Foley et al. |
| 6,298,262 | B1 | 10/2001 | Franck et al. |
| 6,322,567 | B1 | 11/2001 | Mittelstadt et al. |
| 6,459,926 | B1 | 10/2002 | Nowlin et al. |
| 6,493,608 | B1 | 12/2002 | Niemeyer |
| 6,584,174 | B2 | 6/2003 | Schubert et al. |
| 6,609,022 | B2 | 8/2003 | Vilsmeier et al. |
| 6,772,002 | B2 | 8/2004 | Schmidt et al. |
| 6,873,867 | B2 | 3/2005 | Vilsmeier |
| 7,203,277 | B2 | 4/2007 | Birkenbach et al. |
| 7,213,975 | B2 | 5/2007 | Khemakhem et al. |
| 7,227,981 | B1 | 6/2007 | Fleute et al. |
| 7,366,562 | B2 | 4/2008 | Dukesherer et al. |
| 7,463,823 | B2 | 12/2008 | Birkenbach et al. |
| 7,542,791 | B2 | 6/2009 | Mire et al. |
| 7,561,733 | B2 | 7/2009 | Vilsmeier et al. |
| 7,567,834 | B2 | 7/2009 | Clayton et al. |
| 7,599,730 | B2 | 10/2009 | Hunter et al. |
| 7,623,702 | B2 | 11/2009 | Arata et al. |
| 7,697,972 | B2 | 4/2010 | Verard et al. |
| 7,713,205 | B2 | 5/2010 | Fu et al. |
| 7,747,311 | B2 | 6/2010 | Quaid, III |
| 7,751,865 | B2 | 7/2010 | Jascob et al. |
| 7,763,035 | B2 | 7/2010 | Melkent et al. |
| 7,771,436 | B2 | 8/2010 | Moctezuma De La Barrera et al. |
| 7,831,292 | B2 | 11/2010 | Quaid, III et al. |
| 7,840,253 | B2 | 11/2010 | Tremblay et al. |
| 7,843,158 | B2 | 11/2010 | Prisco |
| 7,873,400 | B2 | 1/2011 | Moctezuma De La Barrera et al. |
| 8,010,180 | B2 | 8/2011 | Quaid et al. |
| 8,064,985 | B2 | 11/2011 | Peterson |
| 8,095,200 | B2 | 1/2012 | Quaid, III |
| 8,239,001 | B2 | 8/2012 | Verard et al. |
| 8,287,522 | B2 | 10/2012 | Moses et al. |
| 8,311,611 | B2 | 11/2012 | Csavoy et al. |
| 8,339,447 | B2 | 12/2012 | Riederer |
| 8,394,144 | B2 | 3/2013 | Zehavi et al. |
| 8,412,308 | B2 | 4/2013 | Goldbach |
| 8,498,744 | B2 | 7/2013 | Odermatt et al. |
| 8,509,503 | B2 | 8/2013 | Nahum et al. |
| 8,644,907 | B2 | 2/2014 | Hartmann et al. |
| 8,657,809 | B2 | 2/2014 | Schoepp |
| 8,753,346 | B2 | 6/2014 | Suarez et al. |
| 8,918,212 | B2 | 12/2014 | Larkin et al. |
| 8,992,542 | B2 | 3/2015 | Hagag et al. |
| 8,992,580 | B2 | 3/2015 | Bar et al. |
| 9,082,319 | B2 | 7/2015 | Shimada et al. |
| 9,125,680 | B2 | 9/2015 | Kostrzewski et al. |
| 9,237,861 | B2 | 1/2016 | Nahum et al. |
| 2003/0130665 | A1 | 7/2003 | Pinczewski et al. |
| 2004/0024311 | A1 | 2/2004 | Quaid, III |
| 2004/0111183 | A1 | 6/2004 | Sutherland et al. |
| 2004/0243109 | A1 | 12/2004 | Tovey et al. |
| 2005/0256689 | A1 | 11/2005 | Schulz |
| 2006/0100642 | A1 | 5/2006 | Yang et al. |
| 2007/0002926 | A1 | 1/2007 | McDonald et al. |
| 2007/0013336 | A1 | 1/2007 | Nowlin et al. |
| 2007/0106306 | A1 | 5/2007 | Bodduluri et al. |
| 2007/0142970 | A1 | 6/2007 | Burbank et al. |
| 2007/0156017 | A1 | 7/2007 | Lamprecht et al. |
| 2007/0156157 | A1 | 7/2007 | Nahum et al. |
| 2007/0185485 | A1 | 8/2007 | Hauck et al. |
| 2007/0270687 | A1 | 11/2007 | Gardi et al. |
| 2007/0270690 | A1 | 11/2007 | Woerlein |
| 2008/0033410 | A1 | 2/2008 | Rastegar et al. |
| 2008/0037714 | A1* | 2/2008 | Sakaida ................. A61B 6/032 378/207 |
| 2008/0208212 | A1 | 8/2008 | Camus et al. |
| 2009/0036918 | A1 | 2/2009 | Burgess |
| 2009/0088634 | A1 | 4/2009 | Zhao et al. |
| 2009/0177081 | A1 | 7/2009 | Joskowicz et al. |
| 2009/0245600 | A1 | 10/2009 | Hoffman et al. |
| 2010/0056905 | A1 | 3/2010 | Anderson |
| 2010/0063514 | A1 | 3/2010 | Maschke |
| 2011/0277775 | A1 | 11/2011 | Holop et al. |
| 2012/0310255 | A1 | 12/2012 | Brisson et al. |
| 2014/0350571 | A1 | 11/2014 | Maillet et al. |
| 2014/0371577 | A1 | 12/2014 | Maillet et al. |

FOREIGN PATENT DOCUMENTS

| | | |
|---|---|---|
| EP | 1993482 B1 | 9/2014 |
| FR | 2871363 A1 | 12/2005 |
| FR | 2917598 A1 | 12/2008 |
| JP | 11-309 A | 1/1999 |
| JP | 2001-252268 A | 9/2001 |
| JP | 2008-161266 A | 7/2008 |
| JP | 2009-537915 A | 10/2009 |
| WO | WO94/14366 A2 | 7/1994 |
| WO | WO-9513758 A1 | 5/1995 |
| WO | WO98/38908 A1 | 9/1998 |
| WO | WO02/07612 A1 | 1/2002 |
| WO | WO-2002007612 A1 | 1/2002 |
| WO | WO02/061709 A1 | 8/2002 |
| WO | WO03/043515 A1 | 5/2003 |
| WO | WO-2003043515 A1 | 5/2003 |
| WO | WO2005/032390 A1 | 4/2005 |
| WO | WO2005/122916 A1 | 12/2005 |
| WO | WO-2006075331 A2 | 7/2006 |
| WO | WO2007/113713 A2 | 10/2007 |
| WO | WO2011/063715 A1 | 6/2011 |

OTHER PUBLICATIONS

Kienzle (III) et al.; Total knee replacement; IEEE Engineering in Medicine and Biology; 14(3); pp. 301-306; May/Jun. 1995.

(56) References Cited

OTHER PUBLICATIONS

Troccaz; Capteurs et recalage per-opératoires en robotique médicale (in French w/ Machine Transl. of Intro. and Conclusion); HAL Id: cel-00344721, version 1; pp. 1-32; Dec. 5, 2008.

Cruces et al.; Cooperative Robotic System to Support Surgical Interventions (Chap. 35); In Medical Robotics; Bozovic (Ed.); I-Tech Education and Publishing; pp. 481-490; Jan. 2008.

Danilchenko et al.; Robotic Mastoidectomy; Otol Neurotol; 32(1); pp. 11-16; Jan. 2011.

Haidegger et al.; Accuracy Improvement of a Neurosurgical Robot System; Proc. of the 2nd IEEERAS/EMBS Int'l Conf Biomedical Robotics and Biomechatronics (BioRob); Scottsdale, AZ; pp. 836-841; Oct. 19-22, 2008.

Haidegger, T.; Improving the Accuracy and Safety of a Robotic System for Neurosurgery (thesis); Johns Hopkins University; Center for Computer-Integrated Surgical Systems and Technology; 93 pgs.; May 27, 2008.

Howe et al.; Robotics for surgery; Annu. Rev. Biomed. Eng.; 1(1); pp. 211-240; Aug. 1999.

Li et al.; The application accuracy of the NeuroMate robot—A quantitative comparison with frameless and frame-based surgical localization systems; Comput Aided Surg.; 7(2); pp. 90-98; published online Jun. 21, 2002.

Ortmaier et al.; A Hands-On-Robot for Accurate Placement of Pedicle Screws; Proc. 2006 IEEE Int'l Conf. on Robotics and Automation; Orlando, Florida; pp. 4179-4186; May 15-19, 2006.

Ruby, S.; Miniature robot system for keyhole neurosurgery (thesis); The Selim and Rachel Benin School of Engineering and Computer Science; The Hebrew Univ. of Jerusalem; Jerusalem, Israel; 63 pages; Nov. 13, 2005.

Tovar-Arriaga et al.; Development of a robotic FD-CT-guided navigation system for needle placement R preliminary accuracy tests; International Journal on Medical Robotics and Computer Assisted Surgery; 7(2); pp. 225-236; Jun. 2011.

Xia et al.; An integrated system for planning, navigation and robotic assistance for skull base surgery; in J Med Rob.; (Author Manuscript; 20 pgs.); 4(4); pp. 321-330; Dec. 2008.

"U.S. Appl. No. 13/810,186, Non Final Office Action dated Mar. 30, 2015", 13 pgs.

"U.S. Appl. No. 13/810,186, Notice of Allowance dated Aug. 4, 2015", 15 pgs.

"U.S. Appl. No. 13/810,186, Preliminary Amendment dated Jan. 14, 2013", 10 pgs.

"U.S. Appl. No. 13/810,186, Response filed Jun. 30, 2015 to Non Final Office Action dated Mar. 30, 2015", 13 pgs.

\* cited by examiner

METHOD FOR THE AUTOMATED AND ASSISTED ACQUISITION OF ANATOMICAL SURFACES

CROSS REFERENCE TO RELATED APPLICATIONS

This application is a continuation of U.S. application Ser. No. 13/810,186, filed Jan. 14, 2013, which application is the national phase under 35 USC 371 of International Application No. PCT/FR2011/051747, filed Jul. 20, 2011, which application claims priority to French Patent Application No. 1056428, filed Aug. 4, 2010, all of which are herein incorporated by reference.

BACKGROUND OF THE INVENTION

1. Field of the Invention

The present invention is related to the medical field, in particular in operative methodology during the preparation and carrying out of surgical interventions.

The invention relates in particular to medical imaging and, in the perioperative phase, to the automated acquisition of anatomical surfaces, in particular of a patient's head and face, then the surface resetting of the acquired images with respect to images stored in pre-operative phase.

The invention will find an application in the assistance by robotics for the acquisition of anatomical surfaces and for the surface resetting.

To this end, the present invention relates to a method for automated and assisted acquisition of anatomical surfaces.

2. Description of Related Art Including Information Disclosed Under 37 CFR 1.97 and 37 CFR 1.98

In a known way, during a surgical operation on a patient, in particular within the framework of the neurosurgery at the level of a patient's head, the doctor uses systems providing an assistance, in particular by improving the surgical accuracy. To this end, such systems permit, in the perioperative phase, the acquisition of the anatomical surfaces aimed by the operation, then their resetting with respect to images already recorded, for example previously, during a pre-operative phase during an X-ray examination (CT-scan) or an MRI (stands for In particular, the acquisition consists in identifying the actual position of the patient's anatomical zone, by performing a scanning of the surface of said zone using a pointer, for example in the form of a mechanical point, ultrasonic waves or a laser beam. The system then performs a surface resetting in the form of a comparison between this identification and the images recorded previously in the pre-operative phase, calculating the bringing into correspondence of the existing images with the patient's body at the time of the operation. In brief, for each identified point, an evaluation is performed so as to cause the acquired scatter diagram to correspond to the pre-recorded images.

Therefore, the way of performing the step of acquisition of the anatomical surfaces has a considerable influence on the accuracy of the operation that will follow. Several acquisition systems exist nowadays, which use different techniques for identifying the anatomical surfaces.

A first solution consists in positioning, at different particular places of the zone to be acquired, markers, in the form of a mask or pads, directly glued on the skin. These markers are then identified in the space by scanning with a mechanical point or a transmission/receiving beam, namely a laser.

The main drawback of such a scanning resides in its lack of accuracy, which depends on the way of localizing said markers as well as their number and their spatial distribution on the skin. The resetting resulting from the same is then little reliable, i.e., it exhibits important variations and shifts at the level of the surfaces located between the markers.

In addition, the markers can move, because of the elasticity of the skin, even detach. The placing of the markers also obliges to shave the portion of the cranium.

An alternative solution consists in passing over the anatomical zone with a pointer, the coordinates of which are located in the space, in particular through cameras.

According to an embodiment, said pointer can be mechanical, being in the form of a probe, the point of which enters directly into contact with the skin. Said point is manually displaced from one point to another, namely on the morphologically noteworthy points, and along particular anatomical lines of the zone involved, while its different positions and contact points are recorded in three dimensions.

However, though this technique permits to identify a larger number of points of the surface, it remains limited as to the number of points identified, about one hundred, requiring a restriction of the identification to determined lines and determined noteworthy places of the patient's anatomy. This restriction, due to the intervention by the operator, has automatically an influence on the quality of the subsequent surface resetting. Furthermore, the deformation of the skin during the scanning with the pointer is another cause for inaccuracy.

An alternative resides in a contactless pointer, permitting to obtain a larger number of points identified in a smaller period of time. Such a pointer is in the form of a light-radiation transmitter, such as a laser beam. Said transmitter is held in hand by the practitioner, who scans the anatomical zone with the laser.

A first known device comprises a transmitter in the form of a laser telemeter, the position and the orientation of which are constantly identified in the space, permitting to obtain the coordinates of each point recorded by the telemeter.

However, the accuracy of the identification by the telemeter remains limited. That is why it has been devised to directly record the impact of the emitted laser beam at the level of the skin. To this end, the transmitter transmits, on the one hand, a laser beam in the visible light spectrum, in order to allow the practitioner to display the point of impact and its scanning of the patient's anatomical zone and, on the other hand, a beam of invisible light, such as the infrareds, which are captured by specific sensors. Specifically, the reflection of the infrareds at the point of impact permits to accurately identify the position of said point in the space.

It should be noted that the localization of the telemeter or the point of impact of the laser beam uses an optical triangulation principle using various cameras.

Despite these various evolutions, the existing identification and scanning systems are not completely satisfactory.

Indeed, the scanning always occurs manually, creating a human factor, which reduces the accuracy of the identification, but also its repeatable nature, i.e., the scanning paths remain approximate and completely related to the practitioner.

In order to cope with these drawbacks, it has been devised to couple the transmitter to a robot. Such solutions are described in WO 2009/013406, WO 2005/122916 and WO 2005/032390.

In particular, the transmitter is fixed to the end of a robotized arm, hinged so as to have degrees of freedom of movement in the three dimensions. The position of the transmitter and the data it records are then identified in the space with respect to the reference system of said robotized arm.

In particular, a first previous acquisition of said anatomical surfaces is performed, so as to create a three-dimensional representation in the form of a first digital model; then, a second perioperative acquisition by scanning said surfaces is performed, so as to create a three-dimensional representation in the form of a second digital model; then, said scanning is performed with means for identifying the coordinates of said surfaces, said means being supported by a robotized arm; and finally a bringing into correspondence by resetting said first and second models is performed.

Therefore, one observes that the resetting of the models is not optimal, requiring the intervention of a data-processing operator, in order to try to cause the models to match. When this fails, it is necessary to repeat the scanning operation, increasing that more the duration of the intervention.

In addition, even though such devices permit to avoid depending from the operator, by automating the scanning of the anatomical surface, with a highly reproducible nature, this automation considerably limits the capabilities of adaptation of these devices with respect to the anatomical zone, in particular with respect to the different morphologies of the patients.

Furthermore, in all cases the existing devices use means for navigating within the display of the three-dimensional digital model obtained from the images so acquired. These navigation means necessarily require the identification of the transmitter, as previously evoked, thereafter of the surgical instruments.

SUMMARY OF THE INVENTION

The aim of the invention is to cope with the drawbacks of the state of the art by providing a method for automated and assisted acquisition of anatomical surfaces, which combines the accuracy of a scanning assisted by a robotized arm with the adaptability of a manual scanning, while permitting the acquisition of a large number of points.

In particular, the invention foresees to perform a preliminary scanning manually controlled by the practitioner, with a transmitter supported by said robotized arm, permitting, on the one hand, to determine a specific zone for a subsequent fully automated scanning and, on the other hand, to perform a first surface resetting increasing the accuracy of the final surface resetting.

To this end, in such a method:
a first previous acquisition of said anatomical surfaces is performed, so as to create a three-dimensional representation in the form of a first digital model;
a second perioperative acquisition by scanning said surfaces is performed, so as to create a three-dimensional representation in the form of a second digital model; said scanning being performed with means for identifying the coordinates of said surfaces, said means being supported by a robotized arm;
then
a bringing into correspondence by resetting said first and second models is performed.
Said method is characterized in that the scanning consists of:
performing a preliminary identification of the coordinates of the noteworthy points of said anatomical surfaces by manual displacement, assisted by said robotized arm, of said means for identifying at the level of said noteworthy points, so as to construct a reference frame and to determine a scanning zone for said anatomical surfaces;
creating an intermediate model from said reference frame and at least one of said noteworthy points;
performing a preliminary resetting of said first model with said second model;
performing an automatic scanning of the determined zone.

Thus, the method according to the invention provides an increased accuracy in the scanning being performed and the identification of a larger quantity of anatomical points of the zone involved, with an automated and reproducible accuracy of the path, while adding a manual and adaptable nature through the initial manipulation by an operator.

Another advantage of the present invention resides in the use of a robotized arm, which then serves as a reference frame. The anatomical zone to be scanned, then the model extracted from this acquisition are localized with respect to this reference frame, so that thereafter, after resetting, the same reference frame of the robotized arm serves for positioning the surgical instruments for the operation.

According to other features, said method consists of:
performing an identification of the coordinates of at least three noteworthy points;
determining a fourth point from one of said three noteworthy points by symmetry according to an axis passing through the other two of said noteworthy points; and
determining a reference frame for calculating the path of the automatic scanning, said reference frame being formed of at least two axes, each comprising a pair of said four noteworthy points.

Advantageously, said method consists of performing an identification of the coordinates of at least one central point, said central point being located at the intersection of said axes.

According to one embodiment, the method consists in recording said central point at the level of the first model; and in that said preliminary resetting is performed by bringing into correspondence the central point with at least another noteworthy point.

According to another embodiment, it consists in performing the bringing into correspondence of said first model with said intermediate model by matching said axes.

According to the preferred application, said anatomical surfaces correspond to the face and said axes follow at least partially the nose rim and a frontal line.

According to another facultative feature, the method consists in determining a reference frame centered on said robotized arm.

Further features and advantages of the invention will become clear from the following detailed description of the non-restrictive embodiments of the invention, with reference to the attached figures.

DETAILED DESCRIPTION OF THE DRAWINGS

Figure 1:
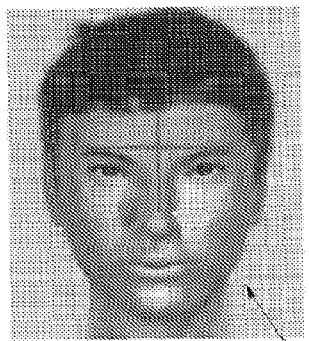
FIGS. 1, 2 and 3 represent a schematic front view of three steps of the method according to the invention applied to a patient's face.

The present invention relates to a method for automated and assisted acquisition of anatomical surfaces.

Specifically, such a method combines a manual intervention with a robotic assistance, then a fully automatic robotized operation.

It should be noted that the anatomical surfaces in the meaning of the invention can comprise any portion of a patient's body. According to the example shown in the figures, according to the preferred embodiment, said anatomical surfaces correspond to the face 1 of said patient.

In a first step, prior to the operation, a first previous acquisition of said anatomical surfaces of the patient is performed. Such a previous acquisition can be obtained by any kind of means, in particular through a scanner or an IRM.

From this previous acquisition, a three-dimensional representation in the form of a first digital model 2 is created.

Then, in the perioperative phase, a second acquisition is performed by scanning of said anatomical surfaces. From this second acquisition, a three-dimensional representation in the form of a second digital model 3 is created.

Finally, a bringing into correspondence by surface resetting of said thus obtained first 2 and second 3 models is performed. In brief, a superposition of said models 2 and 3 is performed in order to cause both representations to coincide, the second model 3 covering said first model 2.

Figure 5:
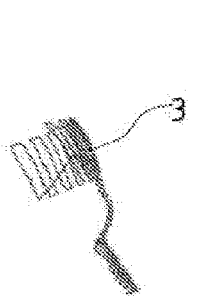
FIGS. 5, 6 and 7 schematically represent three views of the surface resetting of the method according to the invention.
Figure 6:
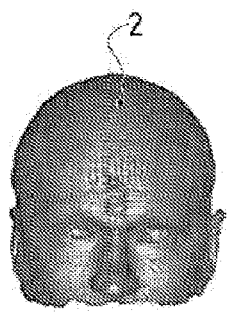
Figure 7:
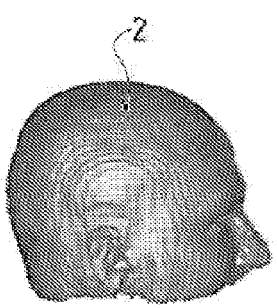

This resetting step is represented in FIGS. 5 to 7, FIG. 5 representing the second model 3, while FIGS. 6 and 7 represent the superposition of said second model 3 on the first model 2, according to a profile view and a front view of the anatomic surface involved, i.e. a patient's head, respectively.

In particular, said resetting can be based on an algorithm for resetting three-dimensional data, referred to as ICP (stands for <<iterative closest point>>). Generally, the ICP algorithm consists in iteratively calculating the rigid transformation matrix (rotation and translation) resetting in the best way two sets of data defined by their coordinates in a three-dimensional identification.

Advantageously, an essential feature of the present invention resides in that said scanning is performed by means for identifying the coordinates of said anatomical surfaces.

In particular, these identification means cam measure in the space and determine the coordinates of points of said surfaces with respect to a reference system.

Preferably, said identification means are supported by a robotized arm. The latter is designed movable and controlled so as to provide it with degrees of freedom of movement according to the three dimensions. Therefore, said reference system, with respect to which the coordinates of the points of said anatomic surface are measured, is determined by said robotized arm.

It should then be noted that the patient is immobilized with respect to the base on which said robotized arm rests and moves.

In this respect, said robotized arm serves as a reference frame, during the acquisition, but also for the subsequent further operations.

In particular, the data-processing means and the calculator associated with said robotized arm permit to centralize the spatial identification of the patient's body, but also of the tools necessary for the acquisition and the scanning of the anatomical surfaces, as the transmitter positioned at the end of said arm, but also for the surgical tools that will intervene in the operative phase.

Therefore, this reference frame permits to reset the information and the coordinates of the patient, of the points, but also of the acquisition and surgery tools, with respect to the pre-operative imaging.

In brief, the robotized arm provides a unique reference system permitting to identify and coordinate in the space, in real time, the various above-mentioned elements. Indeed, the <<modeled chain>> formed by the immobility of the patient's body with respect to the base of the robotized arm, as well as the arm itself until the end of the tool it carries, is sufficient per se to ensure an identification of each of the elements it is comprised of within a reference frame in the space. In order to achieve such a result, it is necessary to initialize such a chain, namely by identifying the elements it is comprised of. Such an initialization operation can be performed prior to the acquisition and during the latter, but also subsequently and during the intervention, through steps of updating of said chain. These updating operations occur automatically depending on the positioning of the tools and elements used, integral with said robotized arm.

Therefore, a repeatable nature intervenes in the positioning and displacement of the tools and elements, while this reproducible aspect could not be contemplated during the fully manual work of a practitioner, making them operator-dependent.

Furthermore, it is also possible to make the patient's body independent from the robotized arm and from its base. Therefore, an acquisition of the position of said patient should be performed in real time, in order to know exactly the changes in same, in order to get adapted to them.

Finally, the end of the robotized arm can also simultaneously carry means necessary for the acquisition and tools for the intervention. Indeed, it is then possible to contemplate, through miniaturized elements and tools, to integrate localization technologies, such as a laser, ultrasounds, a camera, mechanical tools or elements of surface or percutaneous telemetry coupled to tools, namely surgical tools. It is then possible to know in real time the positioning and the displacement of any of these elements, permitting an automation of the movements and paths of each of them, combined with acquisitions and three-dimensional surface resetting operations.

According to one embodiment, said identification means can be designed contactless, namely in the form of a radiation transmitter, for example a light transmitter, such as a laser beam, coupled to a distance sensor. In particular, said identification means can be in the form of a laser telemeter.

Other transmitters can be contemplated, using optical beams, acoustic waves, such as the ultrasounds or radio waves.

Thus, such identification means, located at the movable end of said robotized arm, can move around the anatomical surfaces to be scanned.

In this respect, an essential feature of the invention resides in that the scanning is divided into two successive steps.

A first step of the scanning consists of performing a preliminary identification of the coordinates of noteworthy points of said anatomical surfaces by manual displacement, assisted by said robotized arm, of said identification means at the level of said noteworthy points. This preliminary identification permits to determine a zone for scanning said anatomical surfaces, In brief, the practitioner himself controls the displacement of the identification means, still integral with said robotized arm, in order to position them and to measure the coordinates of the specific points of the anatomical surfaces.

This step is operator-dependent, but sufficiently simple to be implemented in order to ensure a satisfactory reproducibility and accuracy of the coordinates of said noteworthy points.

The second step consists in performing an automatic scanning of the zone determined by said noteworthy points, by means of the robotized arm alone.

Thus, the manual identification permits to improve the automatic scanning by marking and delimiting the zone within which the coordinates will be measured, increasing the accuracy, limiting the risks of extrapolation and providing a capability of adapting the invention to the various morphologies of the anatomical surfaces.

According to a particular embodiment, said manual identification records the coordinates of at least three noteworthy points among 4, 5, 6 or 7 in order to construct a reference frame. A fourth point can be determined by symmetry with respect to three other points already targeted. In particular, in the case of a face, said fourth point can be obtained from one of said three noteworthy points by symmetry with respect to an axis passing through the other two of said noteworthy points. Further noteworthy intermediate points can be identified manually by the practitioner, depending on the cases and the morphology of the anatomical surfaces involved.

Then, a reference frame for calculating the path of the automatic scanning is determined, said reference frame being formed by at least two axes A-A' and B-B', each comprising a pair 4,5 and 6,7 of said four noteworthy points.

Figure 2:
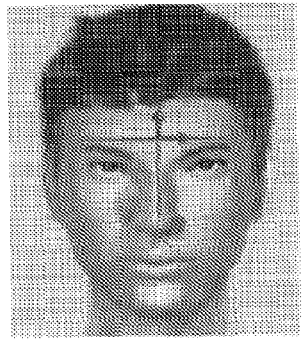
Figure 3:
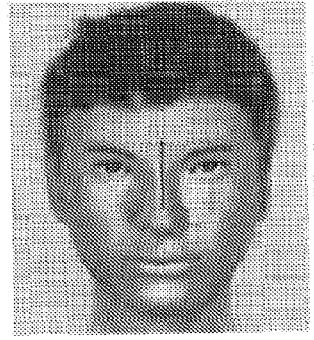

In the exemplary implementation shown in FIGS. 1 to 3, said anatomical surfaces correspond to the face 1. In addition, said axes A-A' and B-B' follow at least partially the nose rim and a frontal line, respectively, the nose rim being substantially vertical, while the frontal line is substantially horizontal. Said noteworthy points can then correspond: for point 4 to the center of the forehead, for point 5 to the end of the nose bone, and for point 6 to a point of the left end of the forehead, while point 7 corresponds to the opposite end.

It should be noted that the points 4 and 5 determine the height of the zone to be scanned, while the points 6 and 7, located on each side of the face 1, permit to determine the width of said zone.

In addition, the invention foresees to perform a first bringing into correspondence with the help of said thus defined frame.

To this end, the invention consists in performing an identification of the coordinates of at least one central point 8. In particular, said central point 8 is located at the intersection of said axes A-A' and B-B'.

Said central point 8 will serve as a center, in order to perform this preliminary surface resetting.

To reach this, said central point 8 should be recorded at the level of the first model 2, i.e. on the imaging performed before the operation.

Then, a three-dimensional intermediate representation in the form of a digital intermediate model is created. In brief, this intermediate model can include any of the noteworthy points 4 to 7, as well as the central point 0 and/or the axes A-A' and B-B'.

Afterwards, a bringing into correspondence is performed through a preliminary resetting of said first model 2 with said intermediate model, by bringing into correspondence said central point 8 and at least another noteworthy point 4 to 7. This intermediate bringing into correspondence can also be performed by means of said so defined reference frame, by correspondence of said axes A-A' and B-B'.

This pre-resetting thus permits to more efficiently adjust the models 1 and 2 during the final resetting.

Said preliminary resetting (and the associated data-processing calculation time) can also intervene during the automatic scanning step.

In this respect, once the scanning zone has been determined, the scanning path is calculated in order to optimize the number and the distribution of the points identified within said zone.

Figure 4:
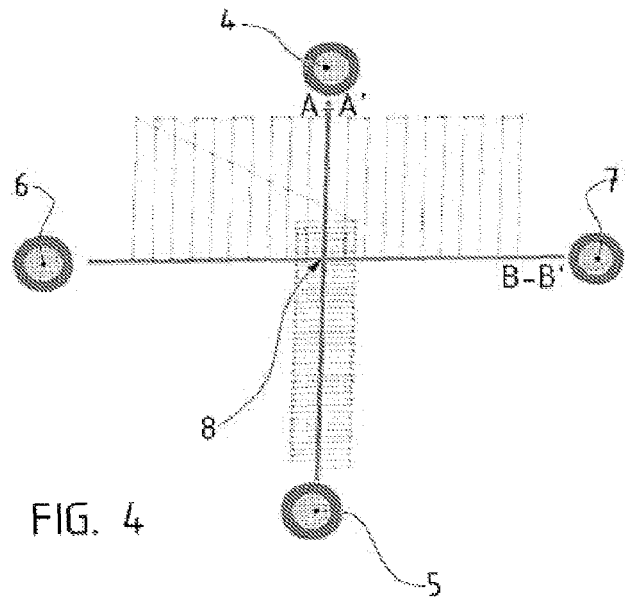
FIG. 4 schematically represents a detailed schematic view of the possibility of the automatic scanning step according to the invention.

A non-restrictive exemplary path is schematically shown in FIG. 4. One observes that the path follows the axis B-B' from the point 6 towards the point 7, in the upper portion of the reference frame, then follows symmetrically the axis A-A' from top to bottom, from the underside of the point 4 to the point 5.

It should be noted that in the example the displacement occurs in the form of a toothed and continuous path. However, any kind of displacement can be contemplated, according to various continuous or discontinuous curves adapted depending on the morphology of the anatomic zone involved.

Furthermore, all the digital data in the meaning of the present invention (models, coordinates or algorithm) and their implementation (recording, modification or display) are processed through adapted data-processing means. The same apply to the programming and the digital controls of said robotized arm.

The method for contactless acquisition according to the invention provides a reliable and reproducible and methodology, quick and easy to be implemented by any practitioner, for an accurate result, avoiding errors related to the operator, while preserving an improvement thanks to the adaptability depending on the practitioner and his medical experience. In particular, the operator can correct the initial path, providing an intelligent and cooperative aspect, but also flexibility with the advantages provided by the strictness and precision of the robotic automatism.

Of course, the invention is not limited to the examples shown and described above, which can have variants and modifications without therefore departing from the framework of the invention.

What is claimed is:

1. A method for peri-operative assisted and automated acquisition of anatomical surfaces, said method comprising the steps of:
   peri-operatively manually displacing a robotized arm supporting a coordinate identifying member;
   manually identifying a plurality of noteworthy points on anatomical surfaces of a patient using the robotized arm and the coordinate identifying member, and recording coordinates of the plurality of noteworthy points and constructing a reference frame;
   creating an intermediate three-dimensional model from the reference frame;
   preliminarily bringing into correspondence the intermediate three-dimensional model with a first three-dimensional model of the anatomical surfaces acquired prior to the manually displacing step from patient medical images;
   determining a path for an automatic scanning process using the reference frame;
   automatically scanning, without manually displacing the robotized arm, a scanning zone along the path using the robotized arm;
   creating a second three-dimensional model from the automatic scanning step; and bringing into correspondence, the second three-dimensional model and the first three-dimensional model.

2. The method of claim 1, further comprising automatically positioning the robotized arm in a position relative to the patient for a surgical intervention.

3. The method of claim 1, wherein peri-operatively manually displacing a robotized arm supporting a coordinate identifying member and recording the coordinates of noteworthy points on anatomical surfaces of the patient comprises recording the coordinates of at least three noteworthy points on anatomical surfaces of the patient.

4. The method of claim 1, wherein the reference frame comprises at least two axes, wherein the two axes each comprise a pair of noteworthy points.

5. The method of claim 1, further comprising creating the first three dimension model from the medical images.

6. The method of claim 1, wherein the path comprises at least two of the noteworthy points.

7. The method of claim 1, wherein the plurality of noteworthy points includes at least one of a center of a forehead, the end of the nose, a point to the left of the forehead, and a point to the right of the forehead.

8. The method of claim 1, wherein the plurality of noteworthy points includes four points, wherein first and second points are in a first axis, and wherein third and fourth points are in a second axis, wherein the first and second axes intersect.

\* \* \* \* \*